Figure 1A:
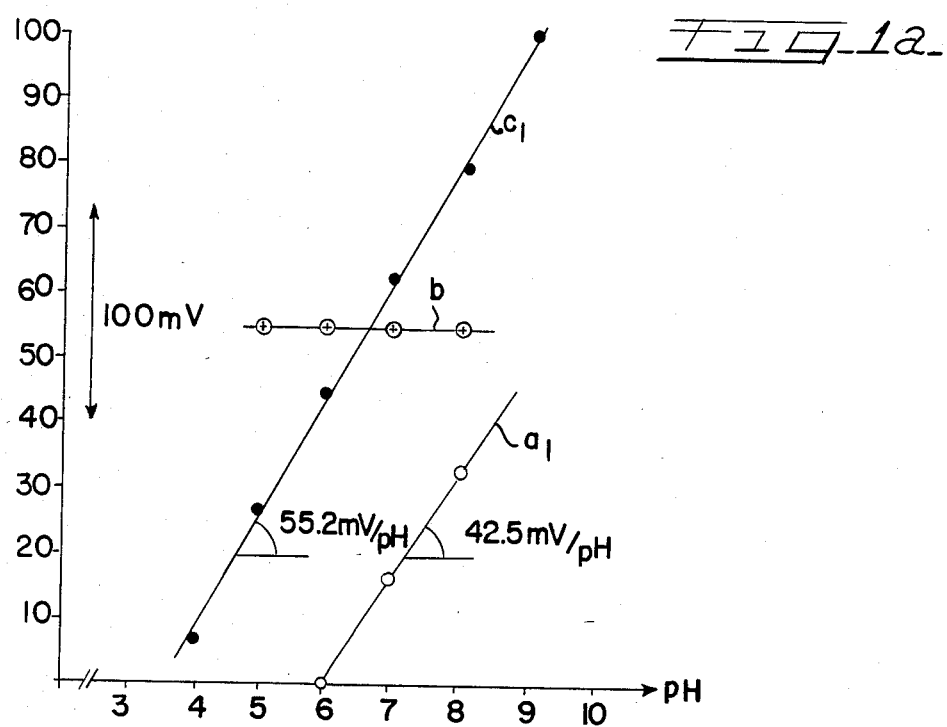

United States Patent [19] [11] Patent Number: 4,552,625
Van Der Velden [45] Date of Patent: Nov. 12, 1985

[54] REFERENCE ELECTRODE ASSEMBLY

[75] Inventor: Paulus M. Van Der Velden, Hengelo, Netherlands

[73] Assignee: Cordis Europa N.V., Roden, Netherlands

[21] Appl. No.: 566,576

[22] Filed: Dec. 29, 1983

[30] Foreign Application Priority Data

Jan. 7, 1983 [NL] Netherlands ......................... 8300057

[51] Int. Cl.$^4$ ....................... G01N 27/46; G01N 27/30
[52] U.S. Cl. ................................... 204/1 T; 204/433; 204/435
[58] Field of Search ................ 204/1 T, 1 H, 433, 435

[56] References Cited

U.S. PATENT DOCUMENTS

| 3,498,899 | 3/1970 | Kater et al. | 204/420 |
|---|---|---|---|
| 3,705,089 | 12/1972 | Grubb . | |
| 3,833,495 | 9/1974 | Grubb . | |
| 3,905,889 | 9/1975 | Macur et al. . | |
| 3,926,764 | 12/1975 | Ruzicka et al. | 204/435 |
| 4,214,968 | 7/1980 | Battaglia et al. | 204/435 |
| 4,240,879 | 12/1980 | Dobson | 204/1 H |
| 4,269,683 | 5/1981 | Dobson . | |
| 4,432,366 | 2/1984 | Margules | 204/435 |

FOREIGN PATENT DOCUMENTS

| 363062 | 7/1981 | Austria . | |
|---|---|---|---|
| 2203521 | 5/1974 | France . | |
| 7113267 | 3/1972 | Netherlands . | |
| 7116613 | 6/1973 | Netherlands . | |
| 1436155 | 5/1976 | United Kingdom | 204/435 |
| 2023845 | 1/1980 | United Kingdom . | |

Primary Examiner—T. Tung
Attorney, Agent, or Firm—Lockwood, Alex, Fitzgibbon & Cummings

[57] ABSTRACT

A new reference electrode assembly is provided that includes a hydrogen ion specific electrode which is encapsulated in a polymer matrix. The bulk of the polymer matrix has an open cell structure within which a liquid is contained as the electrode potential producing agent, while its surface is such that it forms a barrier preventing a free and open connection to the environment of the reference electrode. The reference electrode assembly is especially suitable for in vivo measurements, and it may be designed so that it is substantially insensitive to pH variations of the solution being measured by the instrument of which the reference electrode assembly is a part.

13 Claims, 9 Drawing Figures

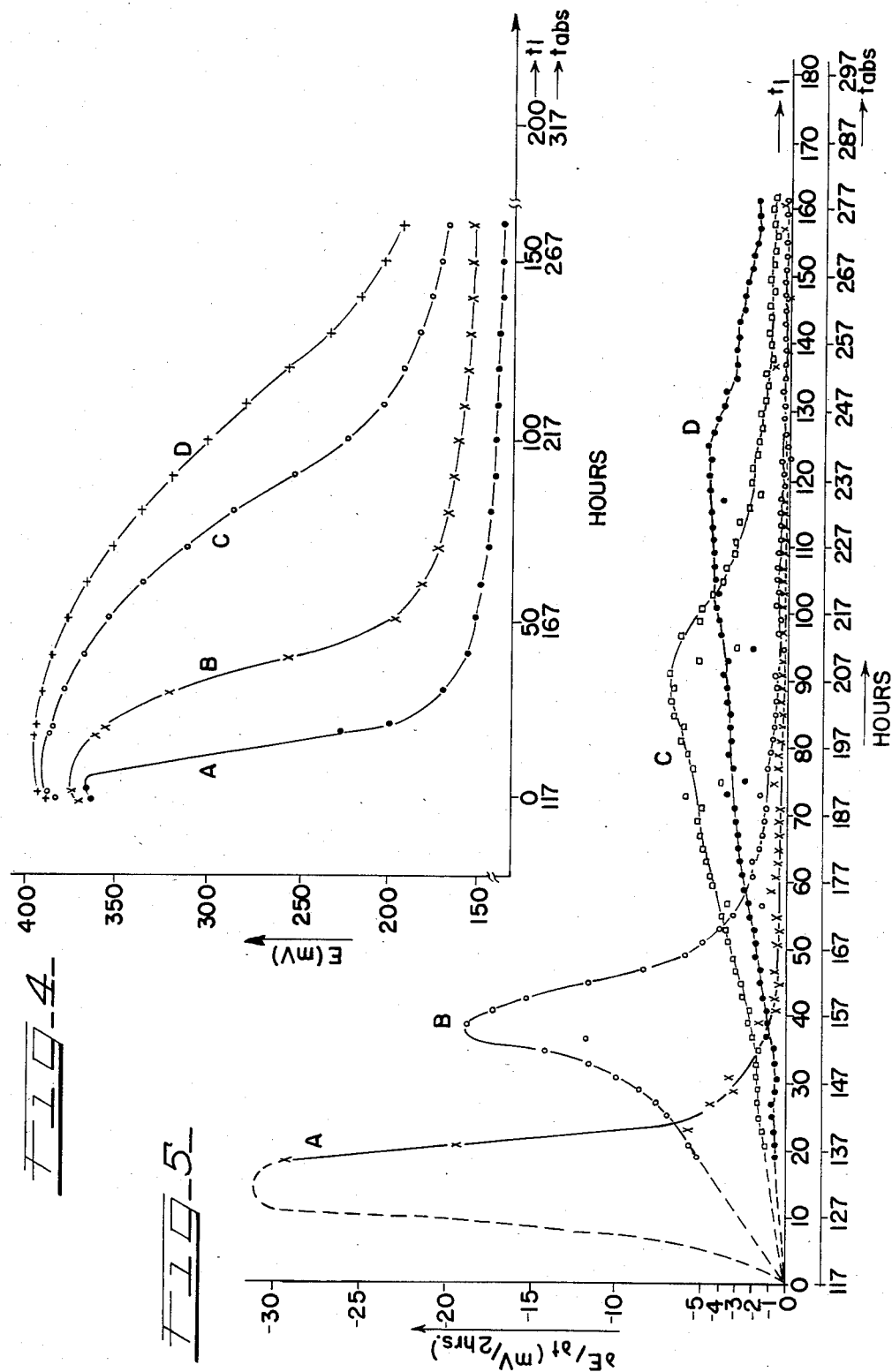

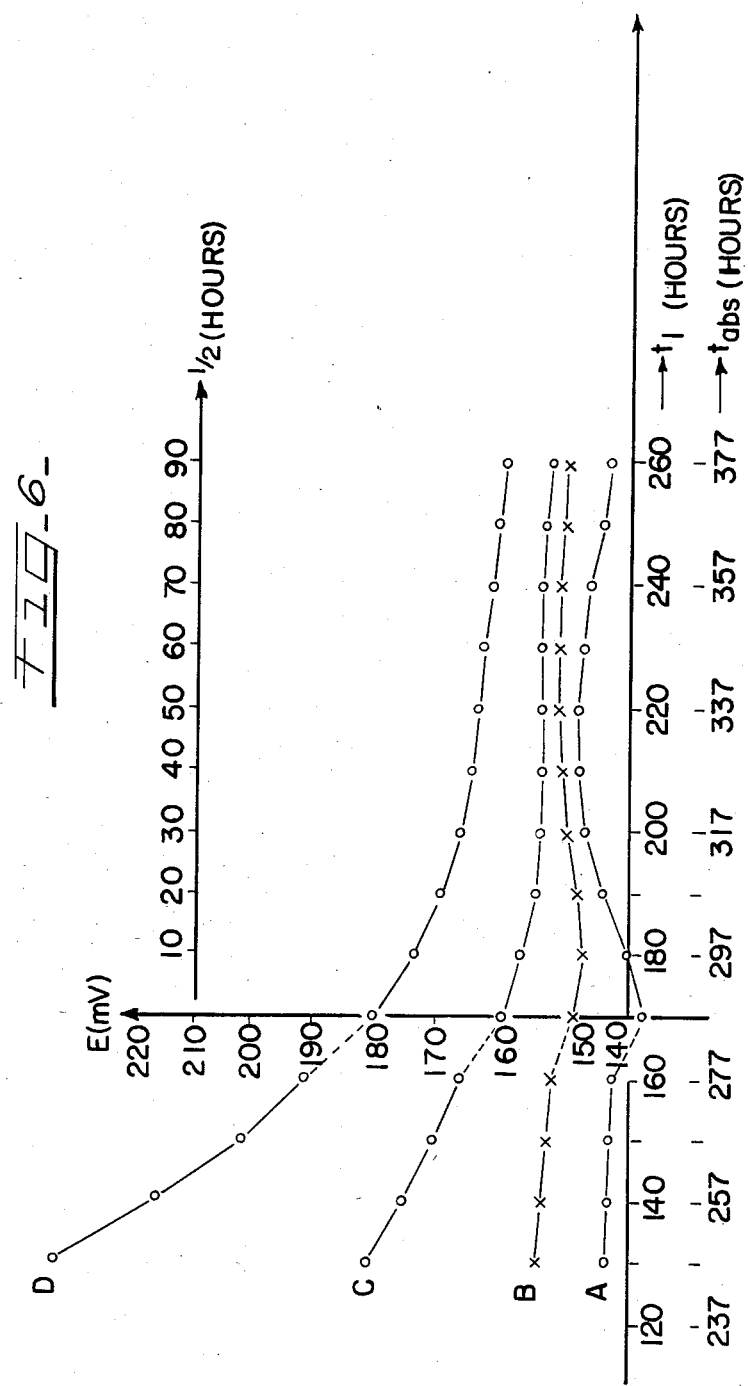

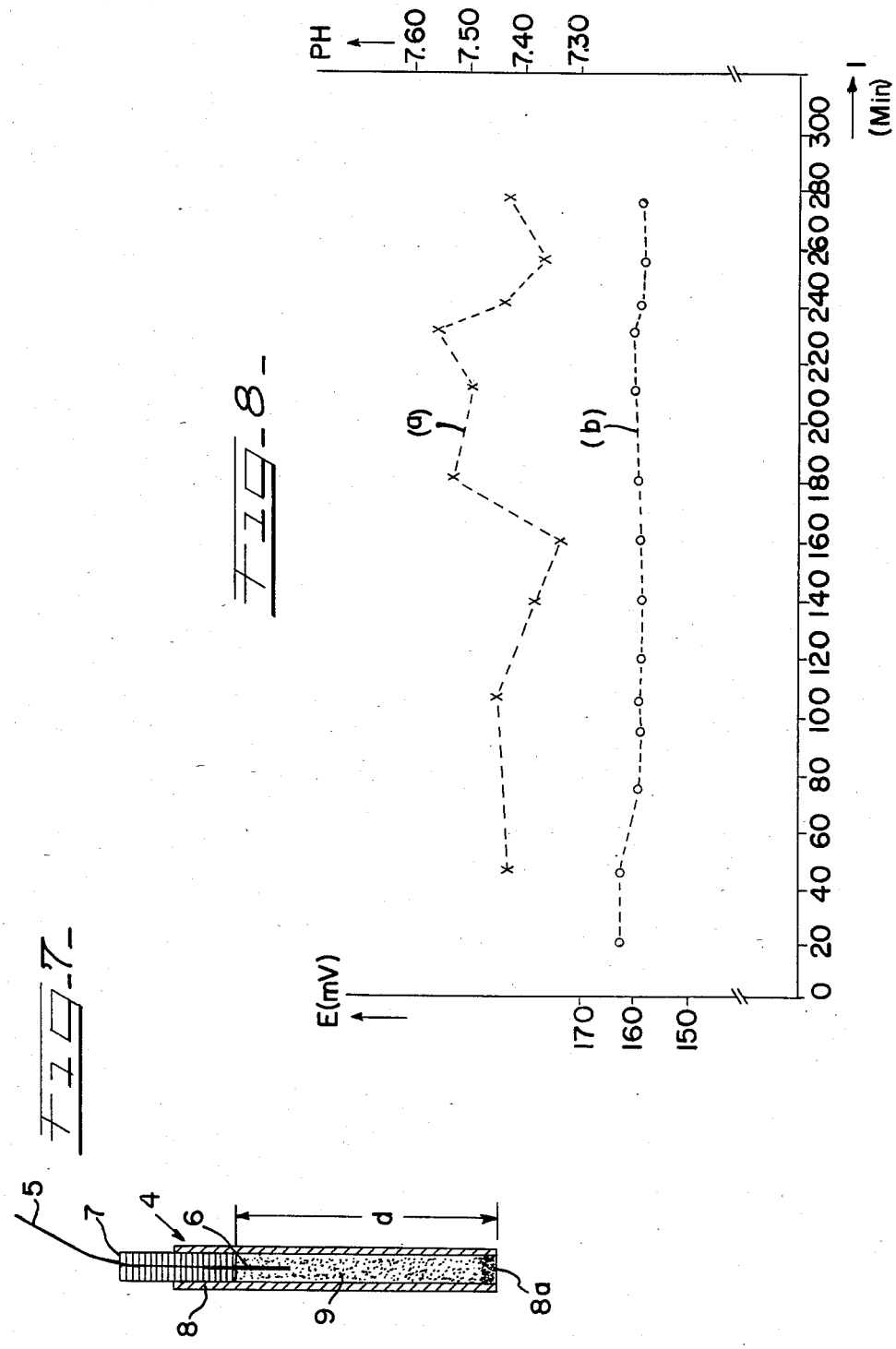

REFERENCE ELECTRODE ASSEMBLY

BACKGROUND AND DESCRIPTION OF THE INVENTION

This invention generally relates to a reference electrode assembly and its use for monitoring liquids that may have a continuously varying composition, more particularly to a reference electrode assembly having a hydrogen ion-specific electrode that is encapsulated within a polymer matrix, the bulk of said polymer matrix having an open-cell structure, the matrix containing a liquid as the electrode potential causing agent while at its surface the polymer matrix includes a structure preventing an open connection with its environment.

Microelectrode instruments are currently used for continuous in-vivo measurement of physiologically important parameters such as pH and pK. In the application of ion specific, active electrodes of this type, it is typically necessary to have a so-called reference electrode available, with respect to which the potential of the active electrode is measured. Reference electrodes should provide a steady reference potential within the electrochemical circuit. Frequently utilized reference electrodes include Ag/AgCl-electrodes and calomel-electrodes. These types of reference-electrodes have only very limited application for in-vivo use, and they are used primarily in conjunction with in-vitro analyses.

Electrodes of the Ag/AgCl type are extremely sensitive to chlorine ions which are present in varying concentrations in fluid to be monitored such as blood. Also, unprotected Ag/AgCl electrodes exhibit insufficient blood compatibility, evidenced by the fact that, when they are contacted with blood, proteins and platelets from the blood soon adhere to the electrode surface, leading to a changing potential and impedance of the reference electrode with time.

In addition to being limited by having similar insufficient blood compatibility, reference electrodes of the calomel type exhibit a further problem if used in-vivo because they contain a relatively concentrated KCl solution. Apart from difficulties brought about by the continuous diffusion of KCl in the bloodstream by electrodes of this type, there exists the danger that even greater concentrations of KCl could enter the blood stream if ceramic frit or the like that maintains same in place becomes broken or cracked. Because the physiology of the human body cannot tolerate high concentrations of potassium in the bloodstream, attempting an in-vivo use of a calomel reference electrode may be injurious or even fatal.

Heretofore, problems of this type have been controlled by the use of so-called adhesive electrodes, typically of the Ag/AgCl type, which electrodes are not placed in the bloodstream but are adhered to the patient's skin, which is used as the ion conducting path. However, these types of electrodes are disadvantageous because of the relatively long distance between the active electrode and the reference electrode and because of the necessity to include a thermostat for the reference electrode. In addition, these measuring systems are difficult to apply in connection with continuous blood analysis in extra-corporal blood circuits such as those utilized during hemodialysis and open-heart surgical procedures.

Austrian Pat. No. 363,062 describes a reference electrode assembly having an electrode which is encapsulated by a polymer matrix that is a gel prepared from a polyacrylamide, a polymethacrylamide, a polyvinyl alcohol, a polyacrylate, a polymethacrylate, polyvinylpyrrolidone or hydroxy ethyl acetate. Such reference electrode assemblies are described to be utilizable as microelectrodes suitable for direct measurement in living cells, it being possible to incorporate a salt or mixture of salts into its polymer matrix. However, this reference electrode is of the Ag/AgCl-type and is, therefore, not based on an electrode reaction comprising hydrogen ions. Furthermore, the salts to be incorporated into the polymer matrix are neutral salts. Accordingly, such reference electrode assemblies exhibit undesirable sensitivity to pH variations in the liquid to be measured.

It is accordingly a general object of the present invention to provide a reference electrode that is especially suitable for in vivo monitoring or measurement of body fluids, such as blood.

Another object of this invention is to provide a reference electrode and method of using same, which use may be as a disposable reference electrode, and which may include applying same directly to the bloodstream for several days in combination with the active electrode.

Another object of this invention is to provide a reference electrode that is insensitive to pH variations in the measuring liquid during extended or varied time periods.

Another object of the present invention is to provide a reference electrode that incorporates a hydrogen ion-specific electrode.

Another object of this invention is to provide a reference electrode assembly in which the electrode member is within a material that takes part in the equilibrium reaction with the hydrogen ions.

Figure 1B:
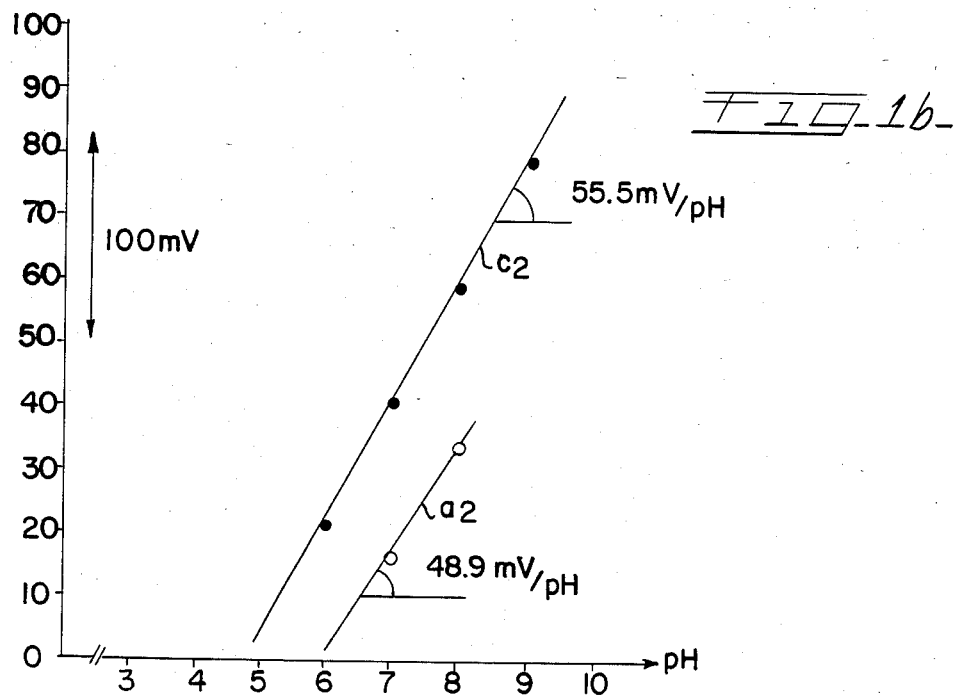
Figure 3:
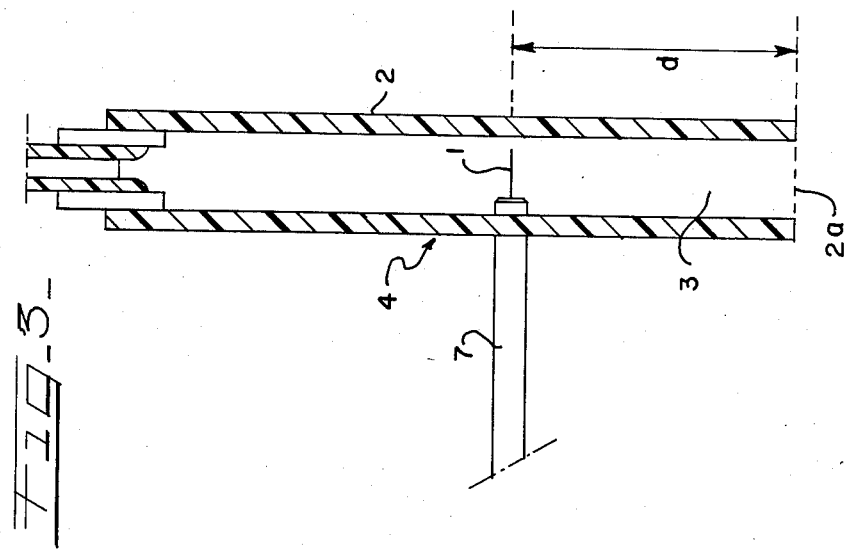
Figure 2:
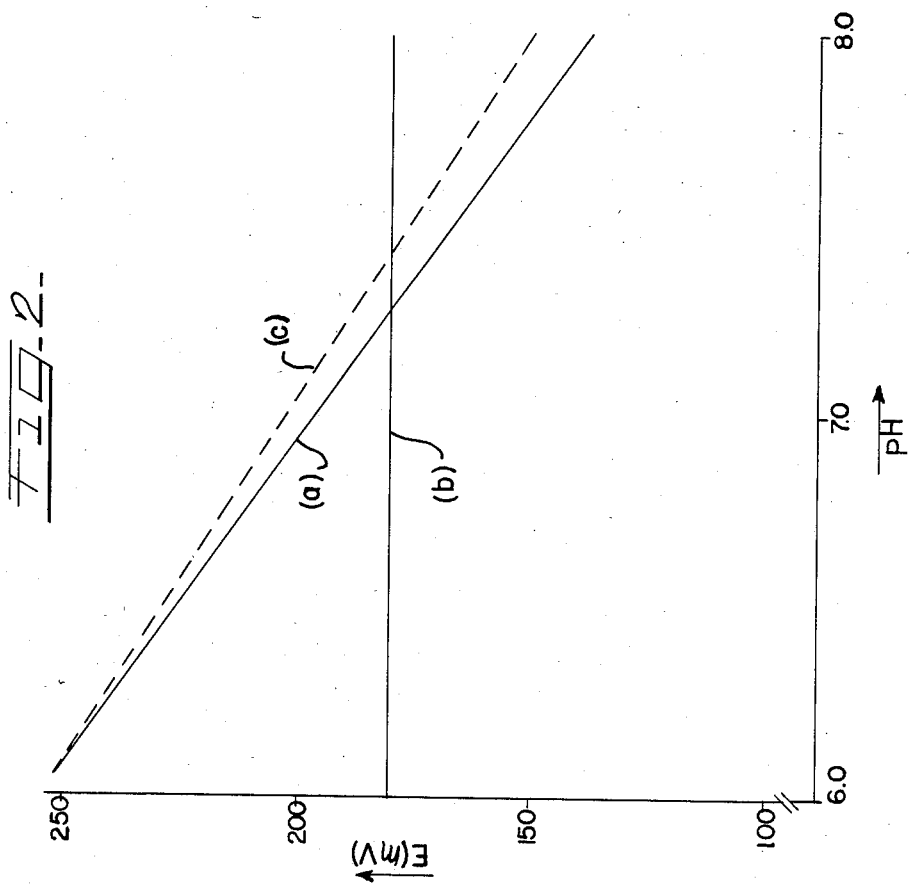

These and other objects, features and advantages of the present invention will be apparent from the following detailed description, including the drawings, wherein:

FIGS. 1a and 1b each give plots of the pH of several solutions being measured versus the voltage deflection generated by a pH-sensitive ion selective field effect transistor (ISFET) having different membranes;

FIG. 2 provides plots of the pH of several solutions being measured versus the potential of the measuring circuit of a pH-sensitive Ir/IrO electrode having different membranes;

FIG. 3 is a sectional view of a reference electrode assembly in accordance with this invention;

FIG. 4 reports plots of the potential of reference electrodes generally according to FIG. 3 versus time;

FIG. 5 provides plots of variations of electrode potentials of various reference electrodes versus time;

FIG. 6 provides plots of the potential of buffered reference electrodes versus time;

FIG. 7 is a sectional view of a reference electrode assembly according to this invention as used in in vivo testing of blood; and FIG. 8 plots results of in vivo testing with the reference electrode assembly of FIG. 7, the plots being of time versus pH variation of the blood (curve "a") and versus the measured electrode potential (curve "b").

The reference electrode assembly according to this invention is generally designated as 4 in FIG. 3 and in FIG. 7. Included is a wire electrode 1 or 6 and a support member such as tube 2 or 8 which generally encloses a polymeric matrix 3 or 9, within which the wire electrode 1 or 6 is imbedded. Typically, the wire electrode 1 or 6 will be mounted by means of an insulating element 7 or the like and will be in electrical engagement with a current conducting wire 5, which may be incorporated within a known type of measuring or monitoring circuit (not shown).

Support member 2 or 8, in order to facilitate in vivo applications in a generally customary manner, includes an open end 2a or 8a by which blood or other fluid enter the electrode assembly 4. Such blood or fluid diffuses from the open end 2a or 8a, through the polymeric matrix 3 or 9, and to the wire electrode 1 or 6. Variations in diffusion times can be effected by modifying the distance "d".

In an important aspect of this invention, the electrode 1 or 6 is of a material exhibiting an electrode reaction which is specific with respect to particular ions such as hydrogen ions, such that the concentration of the specific ions determines the electrode potential. These ion-specific electrodes exhibit potentials with respect to the solution within which they are in contact and that are primarily governed by one particular type of ion, such as the hydrogen ion. Examples of such ion-specific electrodes which may be utilized within the reference electrode assembly 4 according to this invention are an iridium/ iridium oxide electrode (Ir/IrO electrode) or an ion selective field effect transistor (ISFET). A preferred embodiment of the reference electrode according to this invention is characterized by an iridium/iridium oxide pH wire electrode as a hydrogen ion-specific electrode. Such an electrode also fills a biocompatibility requirement which is important for in vivo applications in respect to the ion specific electrode according to the invention.

By encapsulating the electrode according to the invention within a polymer matrix 3 or 9 having an open-pore bulk structure, the liquid in the open pores of the polymer matrix, which acts as the agent for the standard potential, is immobilized. This makes convective liquid transport impossible. For this reason, ion transport through the polymer matrix from, for example, the bloodstream to the electrode (and vice versa) is believed to be only possible by means of diffusion. Because diffusion processes are very slow, mass transport may last about ten hours up to several days, dependent on the length of the diffusion path.

It is important that the polymer matrix 3 or 9 include or be built up from a material having a strong affinity for hydrogen ions, in order that the transport of the hydrogen ions through the polymer matrix will be influenced. Suitable materials in this regard are those that are weak polyelectrolytes, such as cellulose acetate. It is preferred that the wire electrode 1 or 6 be encapsulated by a polymer matrix 3 or 9 that is prepared from cellulose acetate, which is also advantageous for in vivo uses because of its biocompatibility.

In addition, the presence of a buffer solution in the pore structure also influences said hydrogen ion transport. Phosphate buffer solutions are suitable in this regard. Also important for practical application as a reference electrode is that the water-containing polymer matrix is in equilibrium with an isotonic solution such as a physiological phosphate buffer solution.

Based on the aforementioned aspects and mechanisms of the polymer matrix, the period of the time during which the reference electrode according to the invention may be applied in practice is dependent, among other things, on the length of the electrode, on the type of the polymer matrix, and on its structure. As such, the reference electrode according to the invention is adjustable as desired to meet particular needs and is especially suitable to be used within disposable medical devices and articles.

An additional advantage of the reference electrode assembly according to the invention, when it is used as a reference electrode in a complete pH measuring system provided with an iridium/iridium oxide pH wire electrode, is that it exhibits a significantly reduced temperature sensitivity when compared, for example, with a known pH measuring system that includes a silver/silver chloride (Ag/AgCl) reference electrode in association with the iridium/iridium oxide pH wire electrode.

EXAMPLE I

A pH-sensitive ion selective field effect transistor (ISFET) was utilized in testing for the determination of the influence of the type of material of the polymer matrix on the pH-sensitivity of a pH-sensitive indicator such as an ISFET. A series of Merck buffer solutions having pH values varying between 3 and 9 were contacted with the sensor which was tested without a membrane (plots $a_1$ and $a_2$ in FIGS. 1a and 1b) as well as provided with a cellulose acetate membrane (plot b in FIG. 1a) or a cellulose membrane (plots $c_1$ and $c_2$ in FIGS. 1a and 1b). The last mentioned membrane was obtained by hydrolyzing a previously applied cellulose acetate membrane in a 1.0 weight percent NaOH solution for 30 minutes at 60° C.

The results of the measurements, obtained with two ISFET's, are graphically shown in FIG. 1a and FIG. 1b. Along the Y-axis the meter's deflection is plotted in scale divisions, the scale-value of which is presented in mV, while the pH of the buffer solution tested is plotted along the X-axis. Both the cellulose membrane and the cellulose acetate membrane were homogeneous membrane materials, obtained after an evaporation time of 30 minutes. The average pH-sensitivity of the pH-ISFET without a membrane was approximately between 42.5 mV and 48.9 mV for each pH unit that the tested solution varied, which was generally the same as the pH-sensitivity of the pH-ISFET having a cellulose membrane. When provided with a cellulose acetate membrane, however, the sensitivity of the sensor for pH-changes in the pH-range of between 5 and 8 had completely disappeared (FIG. 1a, plot b).

Analogous experiments were carried out with a pH-sensitive Ir/IrO electrode, provided with a homogeneous layer of cellulose acetate. With these experiments, results were obtained which were quite analogous to those obtained with the earlier-described experiments carried out with the pH-sensitive ISFET. These measuring results are presented in FIG. 2. Along the Y-axis, the potential E of the measuring circuit is plotted in mV, when a saturated calomel-electrode is used as the reference electrode. Along the X-axis, the pH values of the particular experimental solutions monitored are plotted. Graph a relates to the pH-sensitive Ir/IrO electrode according to the invention without a membrane, graph b to the electrode provided with a cellulose acetate membrane, and graph c to the electrode provided with a cellulose membrane.

From these results one may calculate and conclude that a cellulose acetate membrane has the ability to reduce the pH-sensitivity of the reference electrode up to more than 85% when compared with a hydrogel-like cellulose membrane, these tests being conducted within the pH range of 6 to 8, which is the physiologically important pH range for blood analysis procedures.

EXAMPLE II

Four reference-electrodes, which in this and following examples are referred to as electrodes A–D, were constucted based on the design as shown in FIG. 3, which is in accordance with the present invention. The electrode 1, which was an Ir/IrO electrode, was radially fitted within the open ended polyvinylchloride tube 2, which is provided with a polymer matrix 3 of cellulose acetate. The distance d between the Ir/IrO-electrode and the matrix-surface was varied for each different electrode. In electrode A, d was 1.0 cm; in electrode B, d was 2.0 cm; in electrode C, d was 3.0 cm; and in electrode D, d was 4.0 cm.

The polymer matrix was applied by filing up each electrode with a 20 weight percent cellulose acetate solution in acetone and then placing the assembly in demineralized water, with the result that a cellulose acetate matrix was formed by coagulation. After the electrodes had been maintained during 117 hours in regularly renewed demineralized water, these reference electrodes were placed in a phosphate buffer with a pH of 7.85. Starting at this moment ($t_1 = 0$ hours) the potentials of the reference electrodes A–D were continuously measured with reference to a saturated calomel reference electrode. All such measurements took place in a measuring arrangement, which was thermostated at 37° C.

The results are graphically presented in FIG. 4. Along the Y-axis the potential in mV is plotted, having used the saturated calomel electrode as the reference electrode, while along the X-axis the measuring period in hours is plotted, calculated either from the beginning of the treatment of the electrodes by regularly renewed demineralized water as the starting point ($=t_{abs.}$) or calculated from the moment when measurement of the reference electrode potential was initiated ($=t_1$). The potential of the electrodes A–D decreased with time, as was expected, which decrease began at a later time as the diffusion path length "d" increased, this diffusion path length being the distance between the electrode and the open end of the tube.

FIG. 5 shows the variation of the electrode potentials (reported in mV per two hours). These values are plotted along the Y-axis while along the X-axis the same divisions as in FIG. 4 are plotted. From these values, one may conclude, that the diffusion front passes the Ir/IrO reference electrode A after 15 hours, the reference electrode B after 38 hours, the reference electrode C after 90 hours and the reference electrode D after 125 hours. From this it may be concluded that the ion-transport through the polymer matrix indeed is mainly diffusion-controlled.

From FIG. 5, one may further conclude that, if the solution to be analyzed undergoes a pH change or more than 3 pH units, the reference electrode according to this example, treated with demineralized water and with $d = 4$ cm, shows a variation of the potential of less than 1 mV per hour during the first 55 hours of its use at 37° C.

EXAMPLE III

After continuously monitoring the electrodes A–D from Example II (with respect to a saturated calomel electrode) in a phosphate buffer solution having a pH of 7.85, the pH of the solution was reduced to 6.81. This experiment is different from that of Example II because the sudden pH-variation is less and because of the presence of a phosphate buffer solution in the polymer matrix when the pH variation was started.

The variation of the electrode potential E of the electrodes A, B and C was less than $\frac{1}{2}$ mV per hour during a period of more than 100 hours. See FIG. 6, wherein $t_2$ along the X-axis represents time in hours, calculated from the moment of the stepwise change of the pH of the measuring liquid from 7.85 to 6.81. The initially larger potential variation of the electrode D is the consequence of the instability of the potential after $t_1 = 167\frac{1}{2}$ hours. Starting with a pH electrode sensitivity of 59 mV per pH unit, this fact means that when applied as a disposable reference electrode, this electrode has a maximum drift of 0.008 pH units per hour, if the pH of the solution being measured is varying stepwise for 1 pH unit and if the electrode potential is stable on the moment of the pH variation.

EXAMPLE IV

In an in vivo experiment, an electrode according to the embodiment of the invention as shown in FIG. 7 was applied to animals. Electrode 4 was composed of an Ir/IrO wire electrode 6, being mounted in element 7 that was made of silastic rubber. The tube 8 was made of polyvinylchloride, and it was filled with a polymer matrix 9 prepared of cellulose acetate. The distance d was 3 cm.

For the in vivo experiment, the electrode was built in a convential flow-through cell (not shown) such that the end of the tube 8 made contact with the blood in the flow-through cell. This cell was taken up in an extracorporal circulation of the blood of a dog. The pH of the blood was varied through external influence. The electrode-potential E was measured with respect to a saturated calomel electrode, which for this experiment was applied under the skin of the test animal.

The results of a representative experiment are shown in FIG. 8; wherein the Y-axis represents the measured electrode potential E in mV with respect to a saturated calomel electrode and the pH of the blood, respectively, while along the X-axis time t in minutes is plotted. Plot (a) shows the pH-variation and plot (b) the measured electrode potential. With a variation of the pH between the values 7.34 and 7.57 during a period of time of more than four hours, the standard deviation of the used electrode combination was 1.1 millivolt.

It is to be appreciated that this invention can be embodied in various forms and therefore is to be construed and limited only by the scope of the appended claims.

What is claimed is:

1. A reference electrode assembly, comprising:
    an ion-specific electrode, said electrode being encapsulated within and contacted by a polymer matrix, said polymer matrix being a weak electrolyte having a strong affinity for hydrogen ions, the bulk of said polymer matrix having an open cell structure which contains a liquid as an electrode potential causing agent and its surface being such that it forms a barrier preventing a free and open connection to the environment of the reference electrode, said polymer matrix being within a support member, wherein said ion-specific electrode is a hydrogen ion-specific electrode.

2. The reference electrode assembly according to claim 1, wherein the hydrogen ion-specific electrode is an iridium/iridium oxide wire electrode.

3. The reference electrode assembly according to claim 1, wherein the polymer matrix is prepared from cellulose acetate.

4. The reference electrode assembly according to claim 1, wherein the hydrogen ion-specific electrode is an iridium/iridium oxide pH wire electrode, and wherein the polymer matrix is a blood compatible polymer matrix.

5. The reference electrode assembly according to claim 1, wherein the polymer matrix includes a pH buffer material.

6. The reference electrode assembly according to claim 1, wherein the hydrogen ion-specific electrode is an iridium/iridium oxide pH wire electrode and the polymer matrix is a cellulose acetate matrix.

7. The reference electrode assembly according to claim 1, wherein the support member includes an opening for access to fluids being monitored.

8. A method for monitoring the pH of fluids, comprising:

encapsulating a hydrogen ion-specific electrode within a polymer matrix which has an open cell structure and a barrier surface, said encapsulating including contacting the electrode with the polymer matrix, and said polymer matrix being a weak electrolyte having a strong affinity for hydrogen ions;

contacting a portion of the polymer matrix with a fluid to be monitored;

diffusing the ions in the fluid through the polymer matrix and to the hydrogen ion-specific electrode; and measuring a parameter of the fluid by utilizing the hydrogen ion-specific electrode within the polymer matrix as a reference electrode.

9. The method of claim 8, wherein said encapsulating step includes filling a support member with a cellulose acetate solution and coagulating same into a matrix.

10. The method of claim 8, wherein said contacting step includes subcutaneous application.

11. The method of claim 8, wherein the polymer matrix is prepared from cellulose acetate.

12. The method of claim 8, wherein the hydrogen ion-specific electrode is an iridium/iridium oxide pH wire electrode.

13. The method of claim 8, further including incorporating a pH buffering material into the polymer matrix.

* * * * *